United States Patent [19]

Hirshorn et al.

[11] 4,407,302

[45] Oct. 4, 1983

[54] CARDIAC PACEMAKER ELECTRODE TIP STRUCTURE

[75] Inventors: Michael S. Hirshorn, Double Bay; Loraine K. Holley, Rockdale; Michael Skalsky, Waverley, all of Australia

[73] Assignee: Telectronics Pty., Ltd., Lane Cove, Australia

[21] Appl. No.: 251,340

[22] Filed: Apr. 6, 1981

[51] Int. Cl.³ ............................................. A61N 1/04
[52] U.S. Cl. .................................. 128/784; 128/419 P
[58] Field of Search ............................. 128/784–786, 128/419 P

[56] References Cited

U.S. PATENT DOCUMENTS

| 3,941,135 | 3/1976 | Sturm et al. | 128/784 X |
| 3,981,309 | 9/1976 | Cannon | 128/786 X |
| 4,030,508 | 6/1977 | Thalen | 128/786 |
| 4,280,514 | 7/1981 | MacGregor | 128/786 |

FOREIGN PATENT DOCUMENTS

| 24963 | 3/1981 | European Pat. Off. |
| 2516848 | 10/1976 | Fed. Rep. of Germany ... 128/419 P |
| 2613072 | 10/1977 | Fed. Rep. of Germany ... 128/419 P |
| 1535210 | 12/1978 | United Kingdom . |
| 1546107 | 5/1979 | United Kingdom . |
| 2040685 | 9/1980 | United Kingdom . |
| 2043453 | 10/1980 | United Kingdom . |
| 2065478 | 7/1981 | United Kingdom . |

Primary Examiner—Lee S. Cohen
Attorney, Agent, or Firm—Finnegan, Henderson, Farabow, Garrett and Dunner

[57] ABSTRACT

A cardiac pacemaker electrode including an electrode tip having an external surface with a concave region formed therein to increase the pacing impedance thereof. Further, the external surface of the electrode tip is roughened, for example by abrading with a jet of glass beads projected under pressure, to increase the microsurface area of the electrode tip and to reduce the sensing impedance thereof.

14 Claims, 3 Drawing Figures

CARDIAC PACEMAKER ELECTRODE TIP STRUCTURE

FIELD OF THE INVENTION

This invention relates with particularity to the structure of an electrode tip for a cardiac pacemaker and processes for making the electrode tip.

BACKGROUND OF THE INVENTION

A goal underlying all medical implants is to extend the implant life in order to minimize the number of times surgery or other implantation techniques must be performed. For example, in the field of cardiac pacemakers, it is a goal to extend the life of the power source in the pacemaker by minimizing the power requirements of the implant. Furthermore, a pacemaker implant that has a reduced power requirement may utilize a reduced capacity battery to give a lifetime performance of equal duration to pacemaker implants currently available with a physically smaller power source. Both of these goals are directed to reducing the power requirements of the implanted pacemaker electrode as much as possible.

The optimization of the lifetime of a pacemaker implant generally requires a compromise among a number of parameters. For example, it is advantageous to maximize the pacing impedance of the electrode at all times after implant. To accomplish such an increase in the pacing impedance of the electrode, it is necessary to reduce the area of the electrode. This must be done in such a way as to minimize the risk of perforation of the heart tissue and of the chance of dislodgement of an implanted electrode.

Indiscriminately decreasing the size of the electrode tip in order to increase pacing impedance has resulted in some prior art electrodes causing tissue trauma during or following implantation. This result followed from a failure to consider carefully the implications of changes in electrode tip size.

Another significant consideration when designing an electrode tip with optimized performance is the sensing impedance of the electrode tip. The sensing impedance, which should be minimized, increases as the surface are of the electrode tip is decreased. Thus, one of the major problems associated with increasing the pacing impedance by decreasing the surface area of an electrode tip has been the probability of an adverse effect on the sensing impedance.

OBJECTS AND SUMMARY OF THE INVENTION

It is an object of the present invention to increase the pacing impedance of a cardiac pacemaker electrode.

Another object of this invention is to decrease the sensing impedance of a cardiac pacemaker electrode.

Still another object of this invention is to reduce the current drain of a cardiac pacemaker electrode on the power supply for the pacemaker.

A further object of this invention is to minimize the risk of perforation of the heart tissue by a cardiac pacemaker electrode tip both during and following implantation.

Additional objects and advantages of the invention will be set forth in the description which follows and in part will be apparent from the description or may be learned from the practice of the invention. The objects and advantages of the invention may be realized and obtained by means of the instrumentalities and combinations particularly pointed out in the appended claims.

To achieve the foregoing objects in accordance with the invention, as embodied and broadly described herein, a pacemaker electrode comprises an electrode tip having an outer surface, an indentation formed in the outer surface to increase the pacing impedance thereof, and at least one roughened portion on the outer surface to increase the microsurface area of the electrode tip substantially to thereby decrease the sensing impedance of the electrode.

A process for forming a pacemaker electrode according to the instant invention comprises the steps of forming an electrode tip, forming an indentation in the outer surface of the electrode tip to reduce the pacing impedance thereof, and roughening the entire surface of the electrode tip to increase the microsurface area thereof and thereby reduce the sensing impedance of the electrode tip.

BRIEF DESCRIPTION OF THE DRAWINGS

The manner in which the apparatus of the present invention is constructed, its mode of operation, and the process for fabricating the instant invention, can best be understood in light of the following detailed description, together with the accompanying drawings, in which.

DETAILED DESCRIPTION OF THE PREFERRED EMBODIMENT

Figure 1:
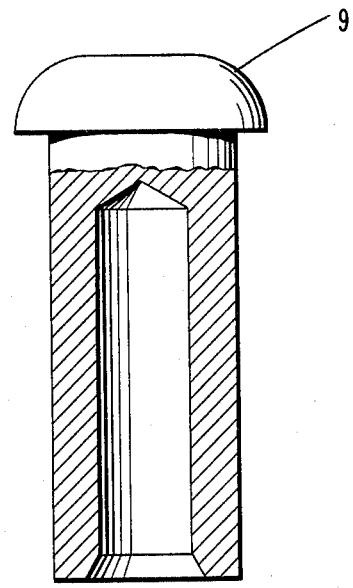
FIG. 1 is a partial cross-sectional view of a prior art electrode tip.
Figure 2:
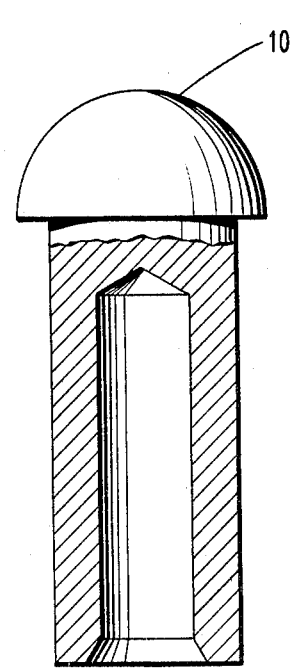
FIG. 2 is a partial cross-sectional view of another prior art electrode tip.

FIGS. 1 and 2 are a partial cross-sectional views of electrode tips previously made by the assignee of the instant invention and sold under the Model Numbers 030-220 and 030-176, respectively. The geometric area, i.e., the area of the outer surface 9 of Model Number 030-220 is approximately 8 mm$^2$ and the area of the outer surface 10 of the Model Number 030-176 is approximately 14 mm$^2$.

Since the pacing impedance of the electrode tip is inversely related to the area of the electrode tip, one of ordinary skill in the art would understand that the pacing impedance of Model Number 030-220 is larger, and hence more desirable than the pacing impedance of the Model Number 030-176. Nonetheless, since the sensing impedance is indirectly related to the area of the electrode tip, the sensing impedance of Model Number 030-176 will be less than the sensing impedance number of Model Number 030-220.

Figure 3:
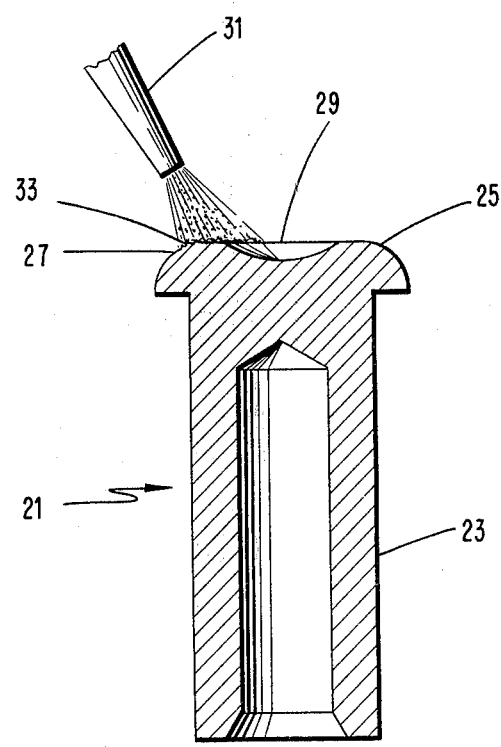
FIG. 3 is a cross-sectional view of the electrode tip of the instant invention.

FIG. 3 is an illustration of the electrode tip structure of the instant invention which comprises an improvement over the electrode tips illustrated in FIGS. 1 and 2. Referring now to FIG. 3, the electrode tip 21 includes a base portion 23 and a head portion 25. In the illustrated embodiment, the top surface of the head portion 25 comprises a convex surface 27 and a concave area 29 is formed in the convex surface 27. The area of convex surface 27 including the concave area 29 is in the range of 4 mm$^2$ to 8 mm$^2$ and the diameter of the head portion 25 is at least 2 mm. The electrode tip 21 is made of platinum or other suitable material.

In the preferred embodiment, the base portion 23 is approximately 4.4 mm in length. The head portion 25 has a height of approximately 0.40 mm and the concave portion 29 has a depth of approximately 0.17 mm. Furthermore, the head portion 25 has a diameter of approximately 2.30 mm and the diameter of the concave area 29 is approximately 1.3 mm. The overall area of the head portion 25 is in the range 4 mm$^2$ to 8 mm$^2$ and shaping the head portion 25 as illustrated in FIG. 3 minimizes the potential for tissue trauma during implantation that was common among prior art electrode tips that were pointed or cylindrical or included acute angles.

While attempting to reduce the sensing impedance of the electrode tip, it was experimentally determined that the sensing impedance was inversely related to the microsurface area of the electrode tip. The microsurface area of an electrode tip comprises the aggregate area of the electrode tip including all indentations, irregularities, and protuberances.

The process developed by applicants for forming electrode tips having an exterior surface, e.g., a concavo-convex surface, with a large microsurface area includes roughening the surface of the electrode by abrasion with glass beads. The surface of the electrode tip is subjected to a blast of glass beads projected from the nozzle 31 at a pressure of approximately 40 psi for approximately 1 to 2 seconds. The diameters of these glass beads may, for example, average 50 microns. This method provides a quick, efficient, and reproducible, roughened finish 33 on all or one or more selected regions of the concavo-convex surface of the electrode tips. The result is a reduced sensing impedance for the electrode tip compared with an electrode tip only having a smooth concave region in a smooth convex surface. One of ordinary skill in the part would be readily aware of alternate means for roughening the surface of the electrode tip, for example, etching with an electrical-etching needle or abrading with minute diamond chips.

The above-described process has been tested by treating 24 electrode tips as illustrated in FIG. 3 with the above-described glass bead roughening method to result in electrode surfaces having a large number of surface irregularities (such as pockets, crevices, protuberances, etc.). These 24 abraded electrode tips, as well as an additional 20 untreated but similarly constructed electrode tips, were then assembled into cardiac pacemaker electrodes according to the usual manufacturing processes. The pacing impedance, the impedance at 10 KHz, and the 50 Hz sensing impedance for a 100 mV signal were measured in vitro in a 9 g/l saline/ethanol (1:1) solution. The measured impedance values are summarized in Tables I and II below. Table I sets forth the impedance results for the electrodes that were not treated with the roughening method and Table II sets forth the impedance results for the electrodes treated with the roughening method.

TABLE I

| IMPEDANCE RESULTS ELECTRODES IN 9g/l SALINE/ETHANOL (1:1) | | | |
|---|---|---|---|
| CODE NO. | $Z_P$ | $Z_{10K}$ | $Z_{50}$ |
| 1 | 562 | 498 | 1852 |
| 2 | 568 | 510 | 1667 |
| 3 | 543 | 493 | 1613 |
| 4 | 568 | 508 | 1786 |
| 5 | 562 | 503 | 1923 |
| 6 | 581 | 508 | 1833 |
| 7 | 581 | 518 | 2041 |
| 8 | 562 | 508 | 1747 |
| 9 | 581 | 516 | 2061 |
| 10 | 549 | 498 | 1754 |
| 11 | 562 | 495 | 1623 |
| 12 | 543 | 490 | 1563 |
| 13 | 568 | 510 | 1852 |
| 14 | 581 | 521 | 1786 |
| 15 | 568 | 508 | 1887 |
| 16 | 549 | 485 | 1613 |
| 17 | 568 | 508 | 2152 |
| 18 | 595 | 508 | 1754 |
| 19 | 510 | 571 | 1852 |
| 20 | 581 | 516 | 1737 |
| MEAN | 564 | 509 | 1805 |
| ±S.D. | 19 | 18 | 157 |
| n | 20 | 20 | 20 |

TABLE II

| IMPEDANCE RESULTS IN 9 g/l SALINE/ETHANOL (1:1) | | | |
|---|---|---|---|
| CODE NO. | $Z_P$ | $Z_{10K}$ | $Z_{50}$ |
| 21 | 526 | 490 | 900 |
| 22 | 562 | 510 | 935 |
| 23 | 581 | 529 | 971 |
| 24 | 588 | 538 | 1000 |
| 25 | 568 | 524 | 971 |
| 26 | 575 | 521 | 1010 |
| 27 | 575 | 508 | 1099 |
| 28 | 568 | 519 | 971 |
| 29 | 575 | 529 | 893 |
| 30 | 543 | 502 | 971 |
| 31 | 549 | 515 | 877 |
| 32 | 568 | 518 | 935 |
| 33 | 609 | 540 | 1111 |
| 34 | 562 | 510 | 1010 |
| 35 | 549 | 500 | 869 |
| 36 | 568 | 515 | 1010 |
| 37 | 555 | 505 | 926 |
| 38 | 581 | 535 | 943 |
| 39 | 555 | 540 | 1010 |
| 40 | 562 | 516 | 1010 |
| 41 | 532 | 505 | 925 |
| 42 | 595 | 540 | 1075 |
| 43 | 521 | 481 | 886 |
| 44 | 568 | 521 | 971 |
| MEAN | 564 | 517 | 970 |
| ±S.D. | 21 | 16 | 66 |
| n | 24 | 24 | 24 |

As evident from above, there was a significant reduction, by approximately 45%, in the sensing impedance, $Z_{50}$, of the electrodes treated by the roughening method when compared to the untreated electrode tips. This procedure experimentally determined that the electrode tips treated with the roughening method exhibited a sensing impedance comparable to a standard 14 mm$^2$ microsurface area tip electrode such as the Telectronics Model Number 030-176 while having the same pacing impedance as a smooth 6 mm$^2$ area tip electrode having a convex surface with a concave portion formed therein.

The following data were experimentally determined in tests utilizing the prior art model electrode having a tip geometric area of 8 mm$^2$ (FIG. 1) and an electrode utilizing a tip as illustrated in FIG. 3 with a geometric area of 6 mm$^2$.

TABLE III

| ELECTRODE CHARACTERISTICS | | FIG. 3 (6 MM²) | FIG. 1 (8 MM²) |
| --- | --- | --- | --- |
| ANIMAL CHRONIC RESULTS | Pacing Impedance (ohm) | 877 | 587 |
| | Threshold Voltage | 0.79 | 1.06 |
| | Sensing Impedance (ohm) | 1086 | 1639 |
| HUMAN ACUTE RESULTS | Pacing Impedance (ohm) | 770 | 608 |
| | Threshold Volt. | 0.3 | 0.62 |
| | R wave Amplitude | 10.2 | 9.34 |

It can be seen that the pacing impedance of the electrode utilizing the 6 mm² a concavo-convex surfaced electrode tip of the instant invention (FIG. 3) was significantly greater than the pacing impedance of an electrode utilizing an electrode tip as shown in FIG. 1.

In summary, by forming a concave area in the convex surface of an electrode tip for a cardiac pacemaker electrode and by roughening the surface by means of etching with glass beads, an electrical needle, or diamond chips, a significant decrease in the sensing impedance is realized while simultaneously the pacing impedance is significantly and advantageously increased. Moreover, the smaller size of the electrode tip of FIG. 3 in combination with its absence of any pointed or acutely angled areas minimizes tissue trauma and the risk of perforation of heart tissue. The result is that a cardiac pacemaker electrode having an electrode tip formed according to the teachings of the instant invention exhibits less current drain on the pacemaker power source and a longer life span than pacemakers utilizing conventional electrode tips without compromising sensing capabilities.

It will be apparent, to those skilled in the art, that modifications and variations can be made in the preferred embodiment and method of manufacture disclosed herein without departing from the scope or the spirit of the invention. Thus, it is intended that the present invention include those modifications and variations which come within the scope of the appended claims and their equivalents.

What is claimed is:

1. A pacemaker electrode having an electrode tip with an external conductive surface for contact with tissue to be stimulated, the improvement comprising means for increasing the microsurface area of said electrode tip to decrease the sensing impedance of said electrode tip, said increasing means comprising at least one roughened area formed on said external surface and at least one concave indentation formed in said external surface for contact with said tissue to be stimulated.

2. A pacemaker electrode as in claim 1 wherein said external surface is convex.

3. A pacemaker electrode as in claim 1 wherein said electrode tip is formed of platinum.

4. A pacemaker electrode according to claim 1, 2, or 3 wherein said roughened area is formed in a portion of said concave indentation.

5. A pacemaker electrode according to claim 1, 2, or 3 wherein said roughened area is formed outside of said concave indentation.

6. A pacemaker electrode according to claim 1, 2, or 3 wherein the area of said external surface including said concave indentation surface is approximately 6 mm².

7. A pacemaker electrode according to claim 1, 2, or 3 wherein the area of said external surface including said concave indentation surface is at least 4 mm².

8. A pacemaker electrode according to claim 1 wherein the area of said external surface is at least 4 mm².

9. An improved pacemaker electrode for stimulating tissue in contact therewith, the electrode comprising:
   an electrode tip having a conductive external surface for contact with the tissue to be stimulated, and
   means for decreasing the sensing impedance of said electrode tip, said decreasing means comprising at least one concave indentation in said external surface for contact with the tissue to be stimulated.

10. A pacemaker electrode as in claim 9 wherein the said external surface is convex.

11. A pacemaker electrode according to claim 9 wherein said electrode tip is formed of platinum.

12. A pacemaker electrode according to claim 9, 10, or 11 wherein said external surface includes at least one roughened portion outside of said concave indentation for increasing substantially the microsurface area of said electrode tip to further decrease the sensing impedance of said electrode tip.

13. A pacemaker electrode tip according to claim 9, 10, or 11 wherein said concave indentation thereof includes at least one roughened portion thereon to increase substantially the microsurface area of said electrode tip to further decrease the sensing impedance of said electrode tip.

14. A pacemaker electrode for electrically stimulating tissue in contact therewith, the electrode comprising:
   an electrode tip having a conductive convex surface for contact with the tissue to be stimulated;
   a concave portion formed in said convex surface to increase the sensing impedance of said electrode tip, the concave surface of said concave portion being exposed for contact with the tissue to be stimulated; and
   a plurality of roughened portions in said convex surface and said concave portion to increase the microsurface area of said electrode tip to decrease the sensing impedance thereof.

* * * * *